(12) United States Patent
Lynn (10) Patent No.: US 11,607,535 B2
(45) Date of Patent: Mar. 21, 2023

(54) NEUTRAL PRESSURE SPLIT SEPTUM LUER ACCESS DEVICE

(71) Applicant: Lawrence Allan Lynn, Columbus, OH (US)

(72) Inventor: Lawrence Allan Lynn, Columbus, OH (US)

(*) Notice: Subject to any disclaimer, the term of this patent is extended or adjusted under 35 U.S.C. 154(b) by 297 days.

(21) Appl. No.: 17/106,595

(22) Filed: Nov. 30, 2020

(65) Prior Publication Data

US 2021/0077803 A1 Mar. 18, 2021

Related U.S. Application Data

(63) Continuation of application No. 14/608,765, filed on Jan. 29, 2015, now Pat. No. 10,881,847, which is a continuation-in-part of application No. 14/009,237, filed as application No. PCT/US2012/031469 on Mar. 30, 2012, now abandoned, said application No. 14/608,765 is a continuation-in-part of application
(Continued)

(51) Int. Cl.
| A61M 39/10 | (2006.01) |
| A61M 39/26 | (2006.01) |
| A61M 39/02 | (2006.01) |
| A61M 39/04 | (2006.01) |

(52) U.S. Cl.
CPC .......... *A61M 39/10* (2013.01); *A61M 39/26* (2013.01); *A61M 39/02* (2013.01); *A61M 39/045* (2013.01); *A61M 2039/1072* (2013.01)

(58) Field of Classification Search
CPC .......... A61M 36/26; A61M 2039/1072; A61M 36/10

USPC .......................................... 604/256
See application file for complete search history.

(56) References Cited

U.S. PATENT DOCUMENTS

| 2,546,672 A | 3/1951 | Clair |
| 4,809,679 A | 3/1989 | Shimonaka et al. |

(Continued)

FOREIGN PATENT DOCUMENTS

WO 2008014448 A2 1/2008

OTHER PUBLICATIONS

Extended European Search Report and Written Opinion dated Jul. 23, 2014 in corresponding European Application No. 12765669.2.
(Continued)

*Primary Examiner* — Phillip A Gray
(74) *Attorney, Agent, or Firm* — Banner & Witcoff, Ltd.

(57) ABSTRACT

A neutral pressure split-septum luer access device is described for receiving a luer lock connector. The septum has a plurality of elastomeric columns projecting laterally within a chamber. Each elastomeric column is under sufficient compression so that the columns are bowed and the column strength is reduced by bowing, but the slit sealing force is high. This configuration places the lower portion of the slit in a tightly sealed configuration which is never-the-less receptive to penetration by the male luer which causes the columns to bow further and collapse precipitously with the elastomeric force of the collapsing mass of the columns being carried distally to displace and pop open the central slit distal the tip of the male luer. The septum further provides a transverse separation between the columns and a distal sealing portion so the force of the displacement force to the sealing portion is reduced.

14 Claims, 14 Drawing Sheets

Related U.S. Application Data

No. 11/805,381, filed on May 23, 2007, now abandoned.

(60) Provisional application No. 61/470,882, filed on Apr. 1, 2011, provisional application No. 60/900,536, filed on Feb. 8, 2007, provisional application No. 60/836,637, filed on Aug. 9, 2006.

(56) References Cited

U.S. PATENT DOCUMENTS

| | | | |
|---|---|---|---|
| 4,895,346 A | 1/1990 | Steigerwald | |
| 5,242,393 A | 9/1993 | Brimhall et al. | |
| 5,456,284 A | 10/1995 | Ryan et al. | |
| 5,474,544 A | 12/1995 | Lynn | |
| 5,578,059 A | 11/1996 | Patzer | |
| 5,957,898 A | 9/1999 | Jepson et al. | |
| 6,171,287 B1 * | 1/2001 | Lynn | A61M 39/02 251/149 |
| 6,485,473 B1 | 11/2002 | Lynn | |
| 6,695,817 B1 | 2/2004 | Fangrow, Jr. | |
| 6,908,459 B2 | 6/2005 | Harding et al. | |
| 7,713,250 B2 | 5/2010 | Harding et al. | |
| 7,717,882 B2 | 5/2010 | Harding | |
| 7,806,890 B2 | 10/2010 | McKinnon et al. | |
| 7,947,032 B2 | 5/2011 | Harding et al. | |
| 7,998,122 B2 | 8/2011 | Lynn et al. | |
| 8,062,266 B2 | 11/2011 | McKinnon et al. | |
| 8,137,303 B2 | 3/2012 | Stout et al. | |
| 8,163,237 B2 | 4/2012 | Crawford et al. | |
| 8,197,452 B2 | 6/2012 | Harding et al. | |
| 8,257,663 B2 | 9/2012 | Crawford et al. | |
| 8,337,483 B2 | 12/2012 | Harding et al. | |
| 8,377,010 B2 | 2/2013 | Harding et al. | |
| 8,540,677 B2 | 9/2013 | McKinnon et al. | |
| 9,481,118 B2 | 11/2016 | Harding et al. | |
| 2005/0256500 A1 | 11/2005 | Fujii | |
| 2006/0163515 A1 | 7/2006 | Ruschke | |
| 2007/0225635 A1 | 9/2007 | Lynn | |
| 2008/0108956 A1 | 5/2008 | Lynn et al. | |
| 2010/0179489 A1 | 7/2010 | Harding et al. | |

OTHER PUBLICATIONS

International Search Report and Written Opinion dated Aug. 3, 2012 in related International Application No. PCT/US2012/031469.

* cited by examiner

Section A

Figure 6

Section B

Section C

Figure 9

Section D

NEUTRAL PRESSURE SPLIT SEPTUM LUER ACCESS DEVICE

CROSS-REFERENCE TO RELATED APPLICATIONS

This application claims the benefit of and is a continuation of U.S. application Ser. No. 14/608,765, filed on Jan. 29, 2015, which is a continuation-in-part of U.S. application Ser. No. 14/009,237 filed on Oct. 1, 2013, which is a Section 371 filing of international application No. PCT/US2012/03149 filed on Mar. 30, 2012, which is a non-provisional of U.S. Provisional Application No. 61/470,882 filed on Apr. 1, 2011. This application also claims the benefit of and is a continuation-in-part of U.S. application Ser. No. 11/805,381 filed on May 23, 2007, which is a non-provisional of U.S. Provisional Application Nos. 60/836,637 filed Aug. 9, 2006 and 60/900,536 filed Feb. 8, 2007. The disclosures of each of the above applications, including any incorporations by reference therein, are hereby incorporated by reference in their entireties, as if fully set forth herein.

BACKGROUND AND SUMMARY OF SELECTED INVENTIVE ASPECTS

Split septum systems have demonstrated superior performance in reducing blood stream infections in clinical trails. Luer access systems using split or pre slitted septum which receive the luer through the slit are disclosed in U.S. patent application Ser. No. 11/928,843, published under US 2008-0108956 (the entire contents of which is incorporated by reference as if completely disclosed herein). This patent application provides background for the present invention. As disclosed in the aforementioned patent, in some instances it may be desirable to mitigate negative pressure within the luer access device while at the same time, mitigate the penetration force of the luer while providing further enhancement to enhanced sealing force when the luer is advanced through the septum. One embodiment of the present invention discloses a slitted elastomeric septum wherein the septum adjacent the slit is compressed by elastic supports which supports are collapsible on advancement of a male luer releasing at least a portion of the compression over a short distance to mitigate the penetration force while providing a high compression force against the outer luer wall upon completion of the insertion of the luer into the thereby still providing a high degree of sealing about the luer for use, as for example, with high-pressure injection.

One embodiment provides mitigation of negative pressure induced by withdrawal of the luer from the valve by the use of collapsing lateral support columns which displace open a fluid chamber distal to the male luer when the male luer is advanced within a slit between the columns, so that the slit enlarges upon insertion and collapses upon withdrawal of the luer to mitigate negative pressure and provides minimal or no flush or priming volume.

BRIEF DESCRIPTIONS OF THE DRAWINGS

These, as well as other objects and advantages of this invention, will be more completely understood and appreciated by careful study of the following more detailed description of the presently preferred exemplary embodiments of the invention taken in conjunction with the accompanying drawings, in which.

DESCRIPTION OF THE PRESENTLY PREFERRED EXEMPLARY EMBODIMENTS

Figure 1:
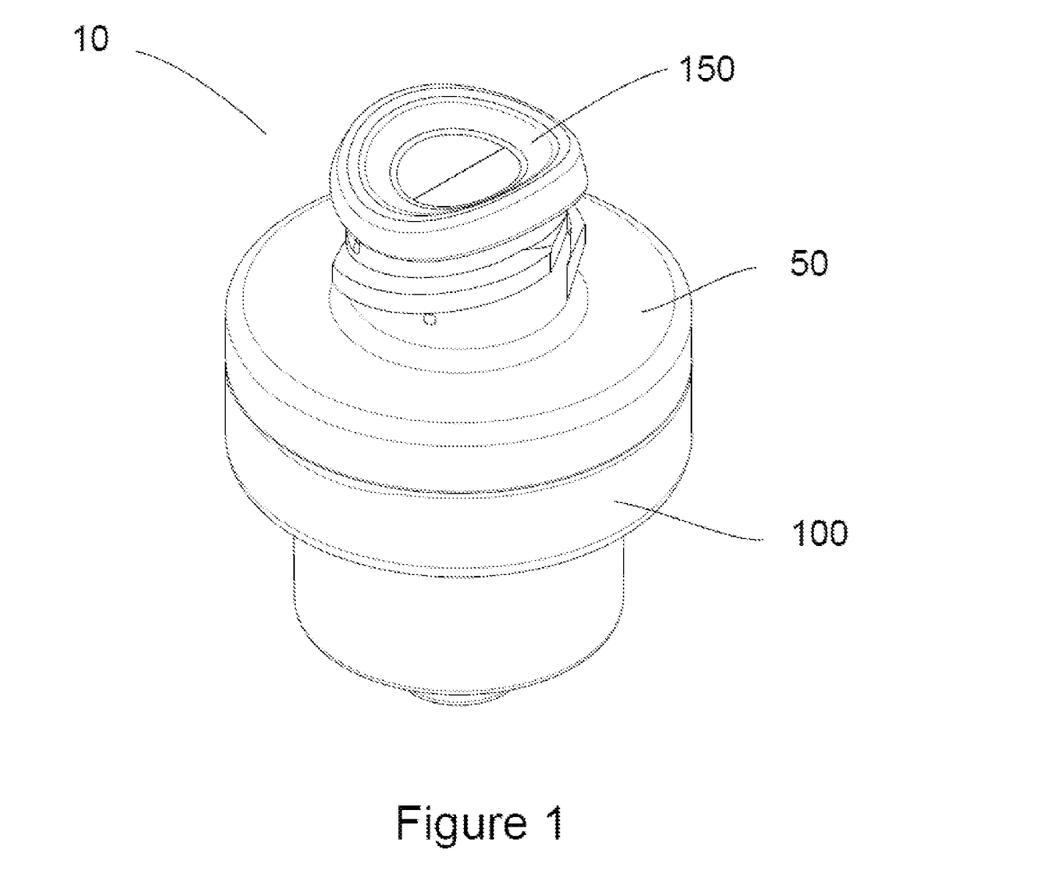
FIG. 1 is a perspective view of a split septum luer receiving valve according to an embodiment of the present invention.
Figure 2:
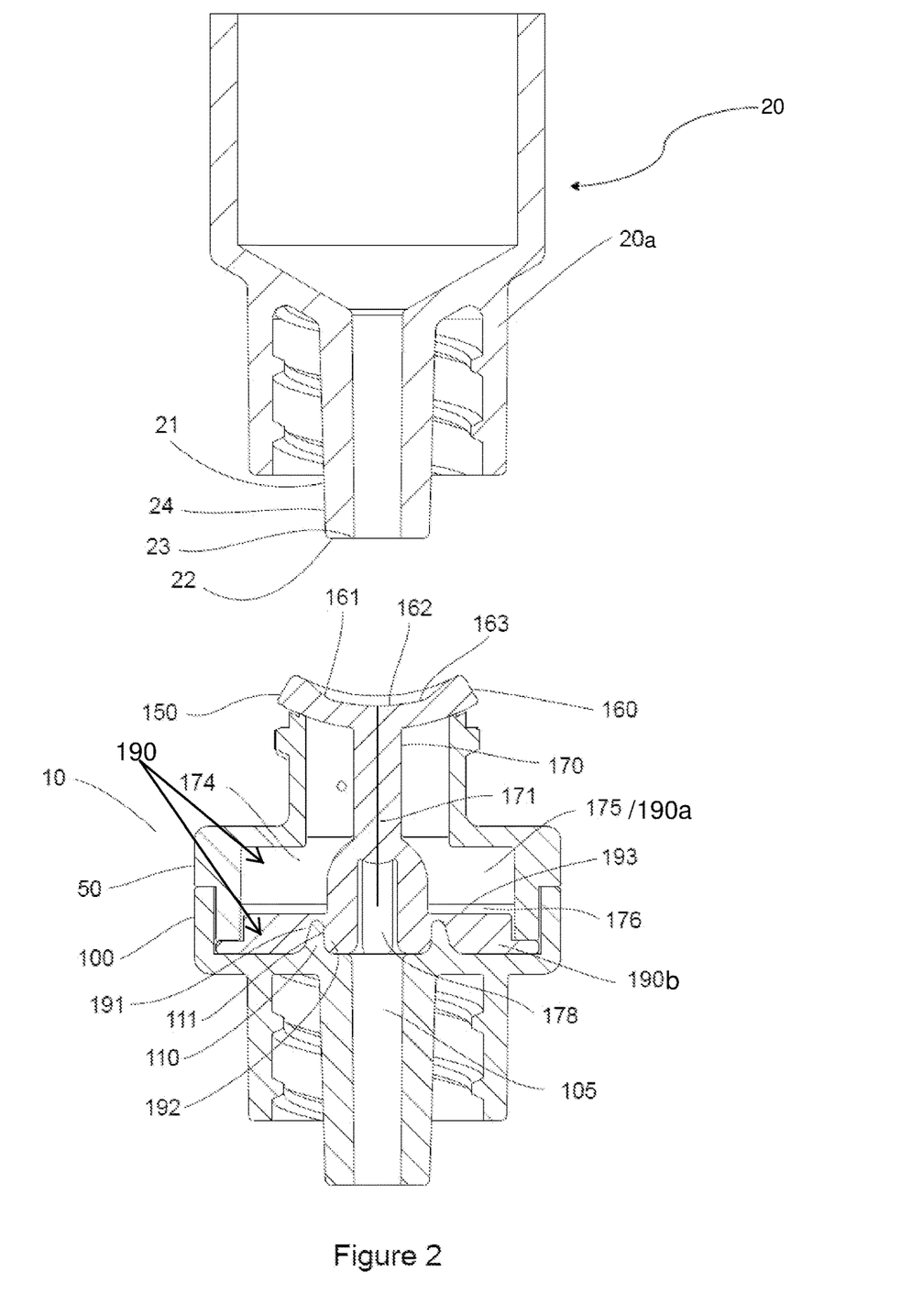
FIG. 2 shows a cross-sectional view of the split septum luer receiving valve of FIG. 1 with a male luer device positioned to be received by the luer receiving valve.

FIG. 1 discloses a split septum luer receiving valve 10 which includes a proximal outer housing portion 50 and a distal outer housing portion 100 and an elastomeric septum 150. FIG. 2 shows a cross-sectional view of split septum luer receiving valve 10 with a male luer device 20 positioned to be received by the luer receiving valve 10. Male luer device 20 comprises a threadable luer lock connector shroud 20a. The elastomeric septum 150 includes an upper portion 160, an extension 170 with a central slit 171 and a lower portion 190. The upper portion 160 includes an outer face 161 configured to receive the distal end 21 of male luer device 20. Outer face 161 has a facial central portion 162 and a facial peripheral portion 163. The upper portion 160 is sloped upwardly at an angle such that the outer edge 22 of the distal end 21 of the male luer 20 engages the outer face 161 and deflects the slit 171 open so that the inner edge 23 of the distal end 21 of male luer 20 does not forcefully engage the outer face 161 but rather passes into the slit 171 as the outer face 161 deflects laterally. When mounted with the housing 50, the facial peripheral portion 163 of the upper portion 160 is deflected upwardly to provided focused compression adjacent the upper surface of slit 171, and this an adjustable angle which allows ready optimization of the compression force at the slit 171, the angle of engagement of the distal end 21 of the male luer 20 and the compression and/or shear force of the septum 150 against the luer 21 during penetration. In one embodiment the angle of upward deflection is about 30-45 degrees but other angles may be used. Because the slit begins to open early, the slit begins to shorten early placing compression on the advancing distal end 21 even at the ends 172 and 173 (FIG. 3) of the slit 171. If desired the slit 171 can be shortened to a length less than the outer diameter of the luer 23 to increase the compression on the external wall 24 at the ends 172 and 173 (FIG. 3) of the slit 171. If desired the slit can be less than 75% of the outer diameter of the luer.

The lower portion 190 includes a proximal portion 190a and a sealing portion 190b. The sealing portion 190b is seated on a surface of distal outer housing portion 100 with an annular projection 110 which mates to a receiving annular recess 191 of lower portion 190. Internal walls of housing portion 100 form a transversely enlarged chamber. Lower portion 190 further comprises an elastomeric annular projection 192 that is a circularly columnar projection of extension 170. Annular projection 110 is similar in profile to annular recess 191 and annular projection 192 such that when mated a seal 111 is effected along the interface of the mating surfaces. Variations of the profile of annular recess 191 and annular projection 192 of septum 150 may be incorporated as viewed in FIG. 5 in order to create an interface of dissimilar characteristics such as shape, diameter, location, surface texture, etc., such that when mated together the rigid nature of annular projection 110 can induce higher normal forces at the interface and a correspondingly higher seal effect.

Figure 3:
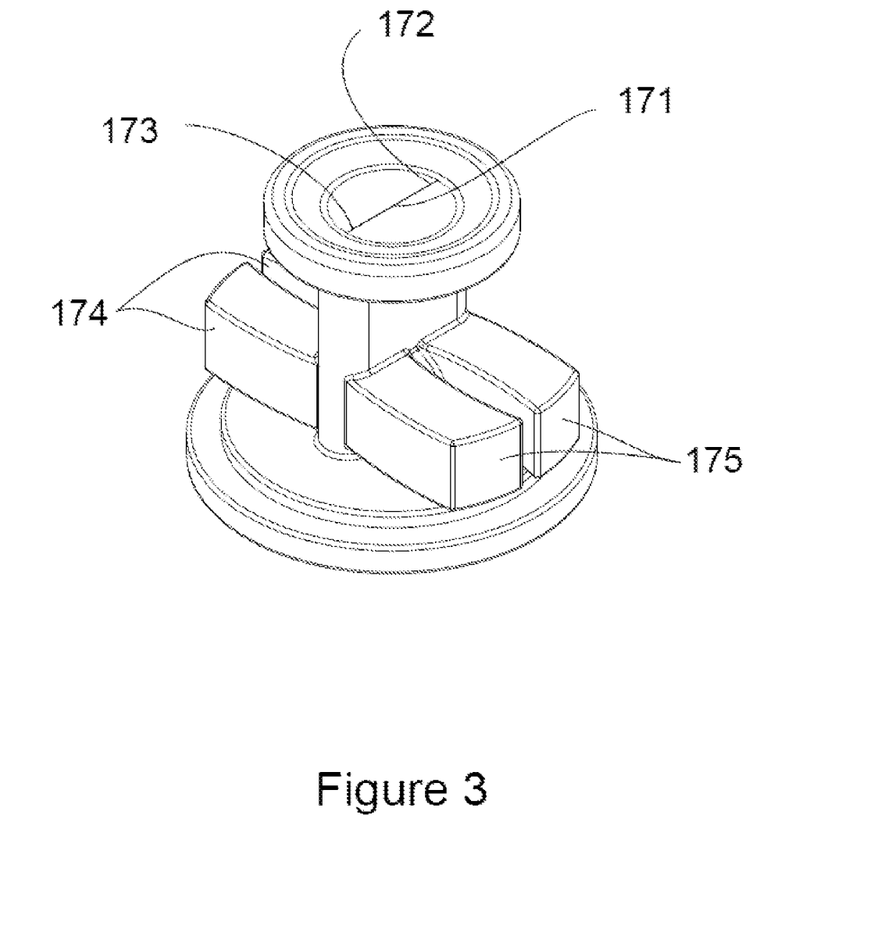
FIG. 3 is a perspective view of one embodiment of a split septum configured for enhanced sealing and displacement mitigation.
Figure 4:
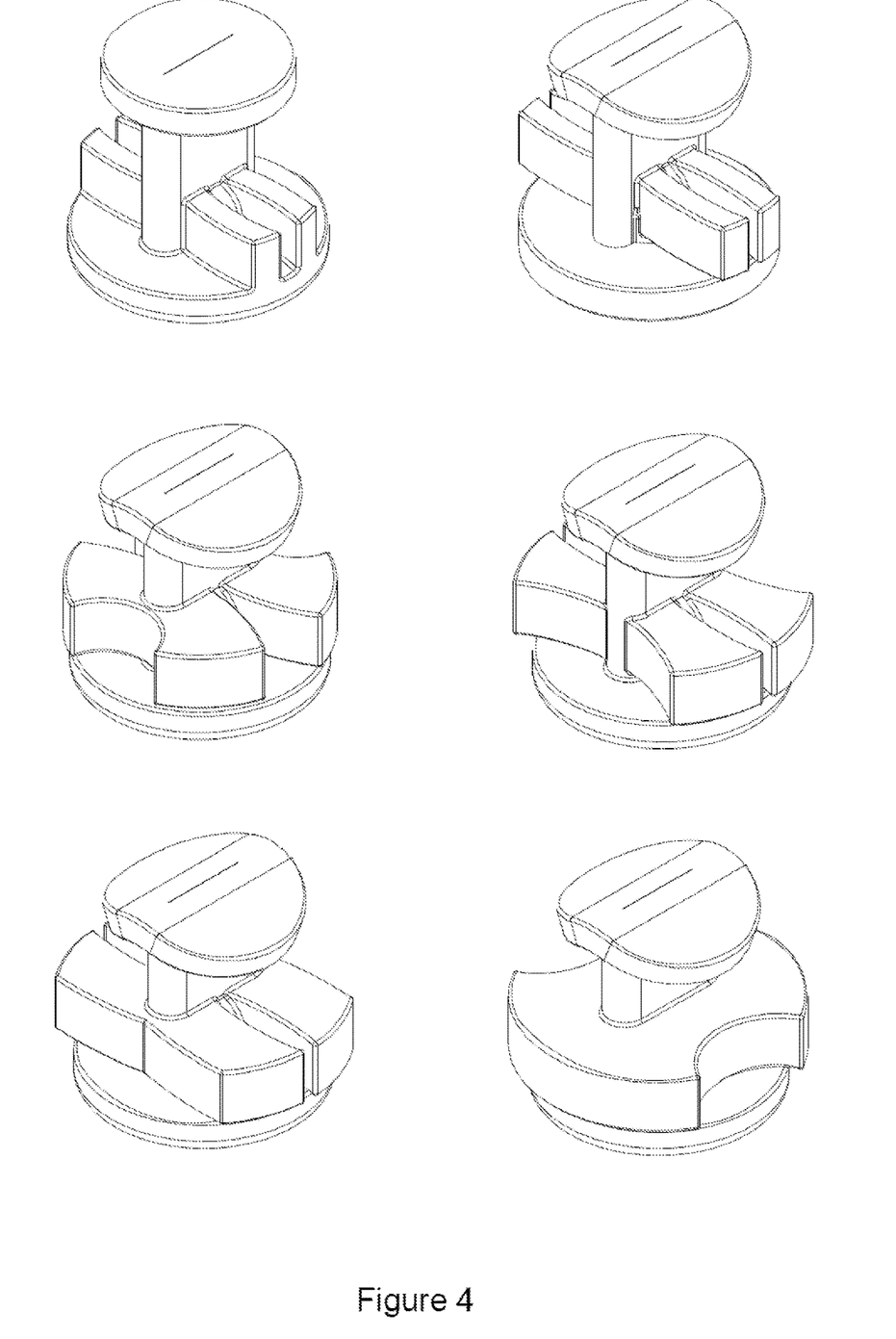
FIG. 4 provides various perspective views of alternative split septums configured for enhanced sealing and displacement mitigation.

Adjacent to extension 170 is an opposing pair of compression inducers comprised of a pair of elastic support columns 174 and 175 directed toward the slit 171 and bowed outwardly to facilitate collapse on compression induced by the male luer as will be described (FIG. 3). The support columns constitute a proximal septum portion 190a projecting laterally, and define a gap or transverse separation 176 in the area between the lower aspect of the support columns and an upper surface 193 of sealing portion 190 (FIG. 2). As a luer penetrates slit 171 the elastomeric material of extension 170 and support columns 174 and 175 are effectively driven radially outward. Gap 176 allows movement of said elastomeric material while isolating movement of elastomeric material associated with sealing portion 190b in order to maintain seal 111 despite the expansive presence of a luer in extension 170. FIG. 4 shows a range of alternative designs of elastic support columns.

Figure 5:
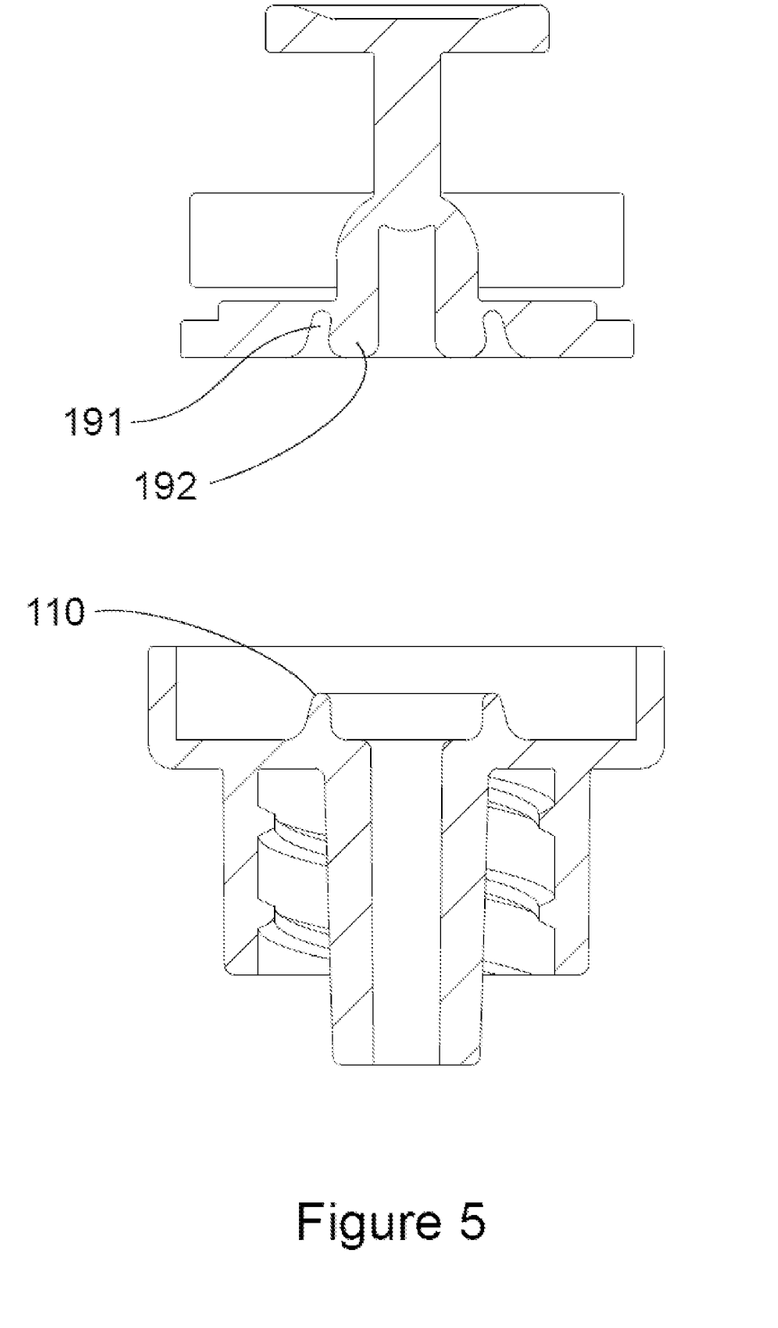
FIG. 5 shows a cross-sectional view of a split septum and the lower housing into which the septum is mounted.
Figure 6:
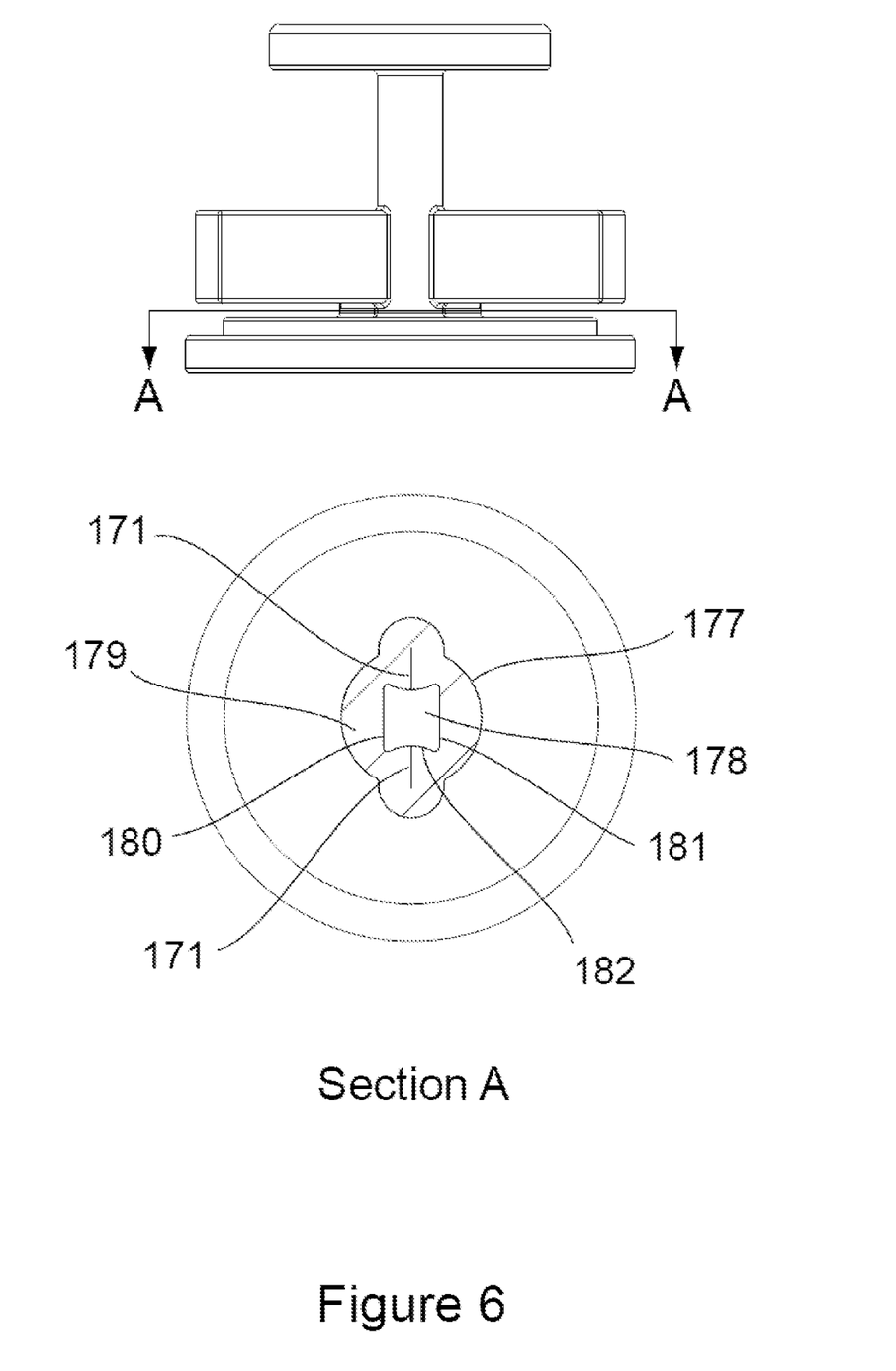
FIG. 6 shows a side view of the septum and cross-sectional view through section A-A of the septum.
Figure 7:
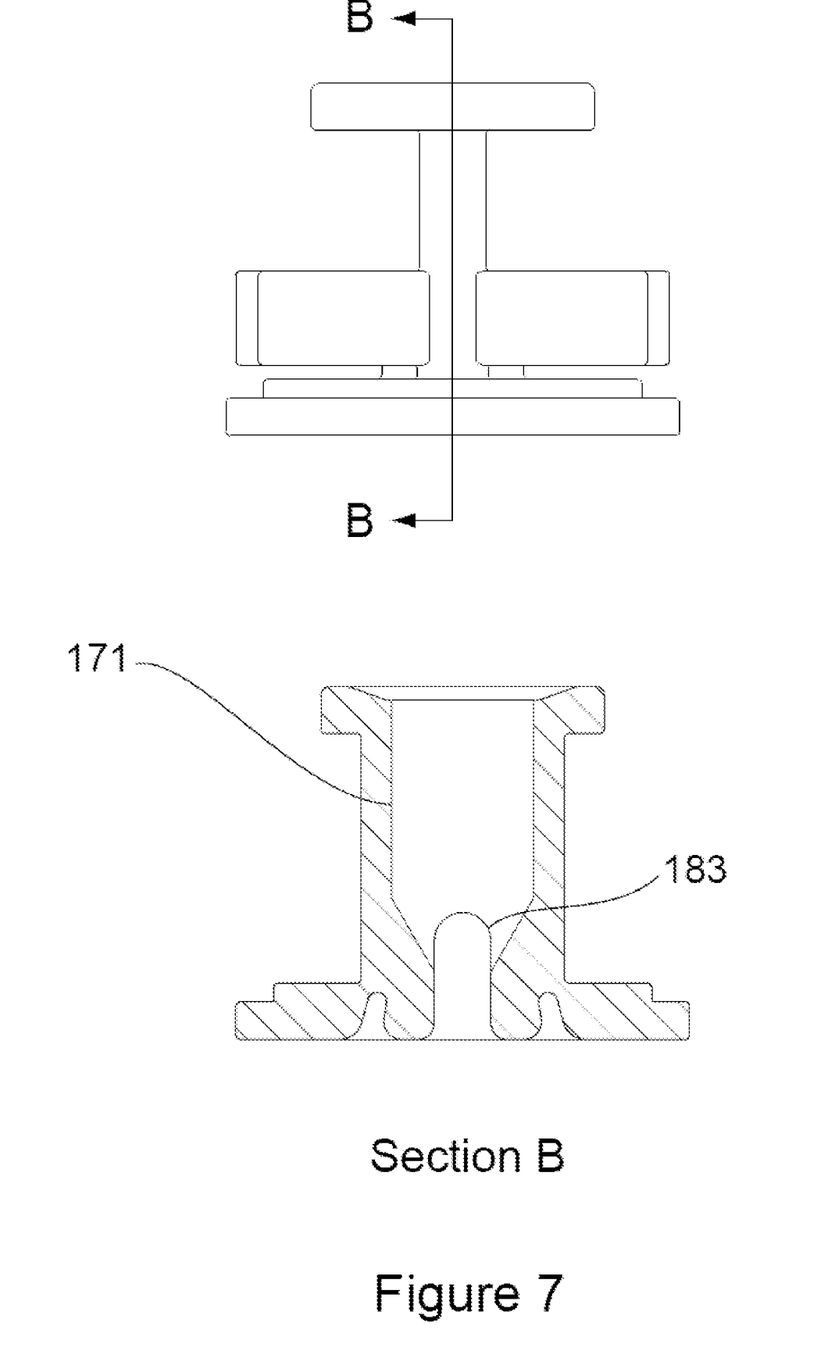
FIG. 7 shows a side view of the septum and longitudinal sectional view through section B-B of the septum.

The cross section of extension 170 is generally elongate in the upper aspects of the extension. Extension 170 transitions from a generally elongate shape to a generally cylindrical shape in such a way that the lower portion of extension 170 contains a cylindrical region 177 having a hollow central core 178 (FIG. 6). The hollow central core may be substantially equivalent in shape to the cylindrical form adjacent to it such that a uniformly thick elastomeric wall 179 is defined. In a preferred embodiment the hollow central core 178 is defined by two opposing substantially parallel and planar surfaces 180 and 181, separated by a continuous curved surface 182. As viewed cross-sectionally coplanar to slit 171 (FIG. 7) the hollow central core is defined as having a dome shape 183. Curved surface 182 from FIG. 5 is further defined by being contoured to the dome shape 183 thereby defining it as a continuous extruded shape following the contour of dome shape 183. Slit 171 that extends from the outer face 161 of upper portion 160 through extension 170 and terminates generally within hollow central core 178 will effectively slice through a measure of the continuous extruded curved surface of 182 (FIG. 6).

Thus, curved surface 182 is generally transverse to slit 171 and surfaces 180 and 181 are parallel and planar to slit 171 as seen in FIG. 6. Curved surface 182, once generally and partially bisected by slit 171, is designed and configured generally to act as a self closing seal with duckbill type characteristics such that fluid pressures associated with use of the luer receiving valve will promote self closing forces on the interface of the slit 171 to the continuously extruded shape of curved surface 182 within hollow central core 178. Further, owing to the continuously extruded shape of curved surface 182 the duckbill type characteristics are displayed similarly continuously along the entirety of curved surface 182 regardless of whether any given portion of curved surface 182 is bisected by slit 171 or not. Thus variability associated with the depth of the slit as a function of manufacturing processes will not substantively affect the viability of the self sealing characteristics of curved surface 182.

Figure 8:
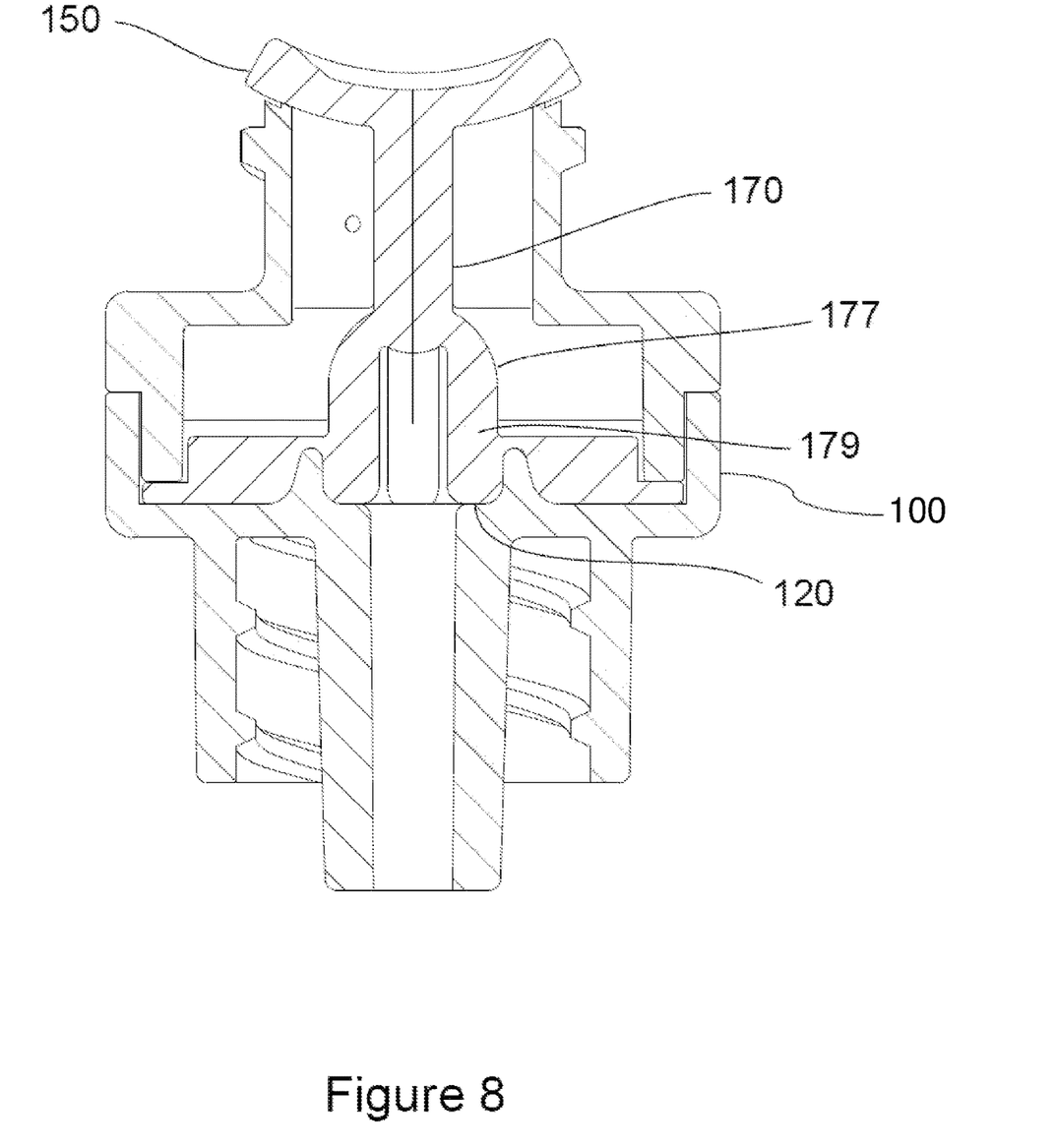
FIG. 8 shows a longitudinal section view of a split septum luer receiving valve according to an embodiment of the present invention.

In the preferred embodiment, as viewed in FIG. 8, the luer receiving valve is designed and configured for the elastomeric material of septum 150 to be displaced laterally as a luer is received. Correspondingly the luer receiving valve of the preferred embodiment has been designed and configured to minimize or eliminate proximal translation of the elastomeric material of septum 150 as a luer is received. The cylindrical region 177 of the lower aspect of extension 170 is substantially seated onto surface 120 of housing 100 such that a penetrating luer is incapable of downwardly displacing the elastomeric material of extension 170 with further collapsible resistance being contributed by wall 179.

Figure 9:
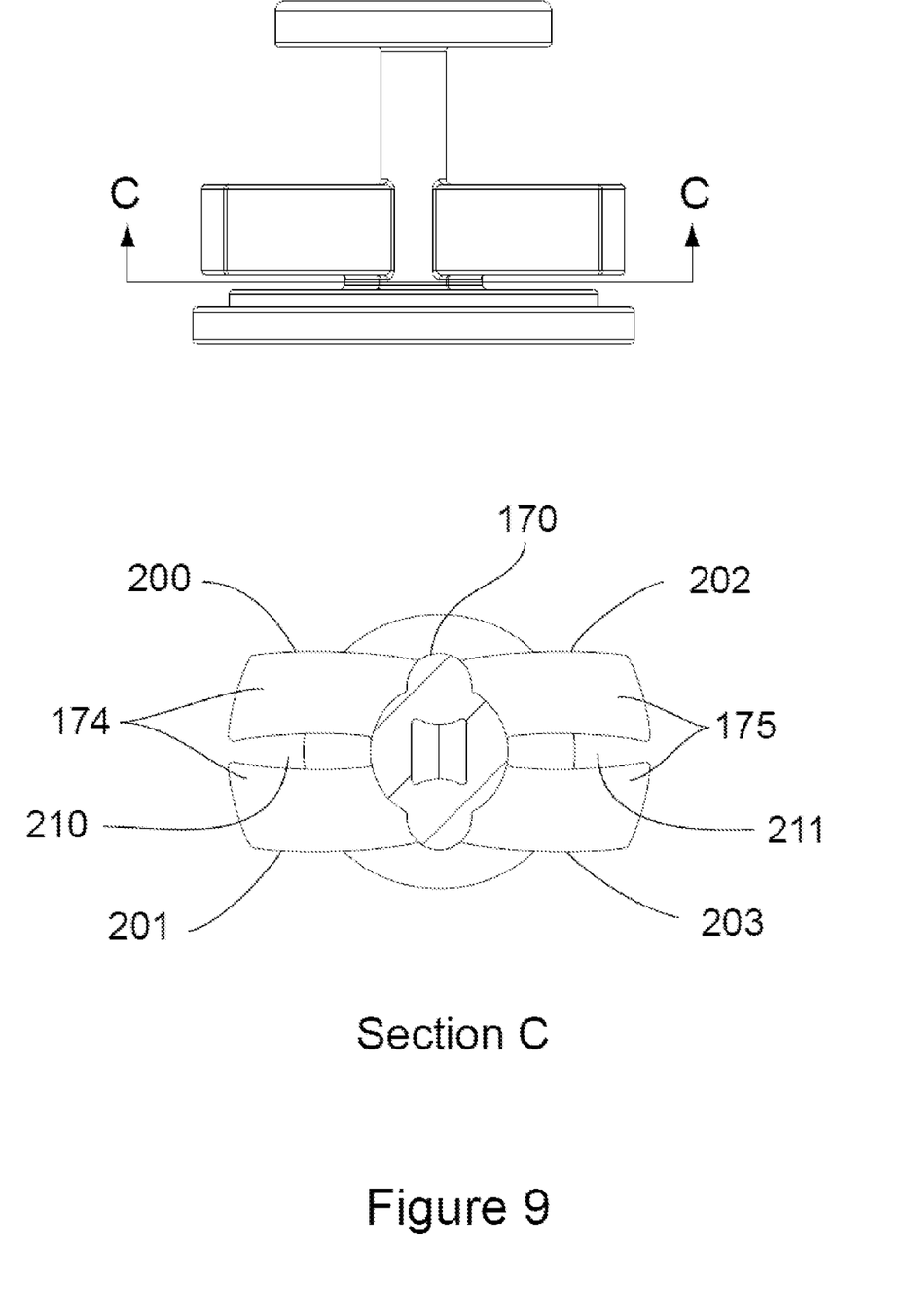
FIG. 9 shows a side view of the septum and longitudinal sectional view through section C-C of the septum.

Elastomeric support columns 174 and 175, as described earlier, are driven radially outwardly as a luer is introduced into slit 171. As viewed cross-sectionally in FIG. 9 the columns have outward facing curved surfaces 200, 201, 202 and 203 respectively and each pair of columns has a gap 210 and 211 therebetween. Gaps 210 and 211 work in concert to allow the cylindrical nature of an advancing luer tip to displace the elastomeric material of extension 170 and support columns 174 and 175 radially outwardly in a way that selectively lowers the force of penetrating said luer into extension 170. Curved surfaces 200, 201, 202 and 203 also work to reduce forces of luer penetration by being biased such that they buckle away from each other in a manner consistent with gaps 210 and 211 enlarging as a result. Advantageously, in this configuration, the columns are prevented from bucking in towards each other on luer penetration which would arbitrarily increase luer penetration forces.

Figure 10:
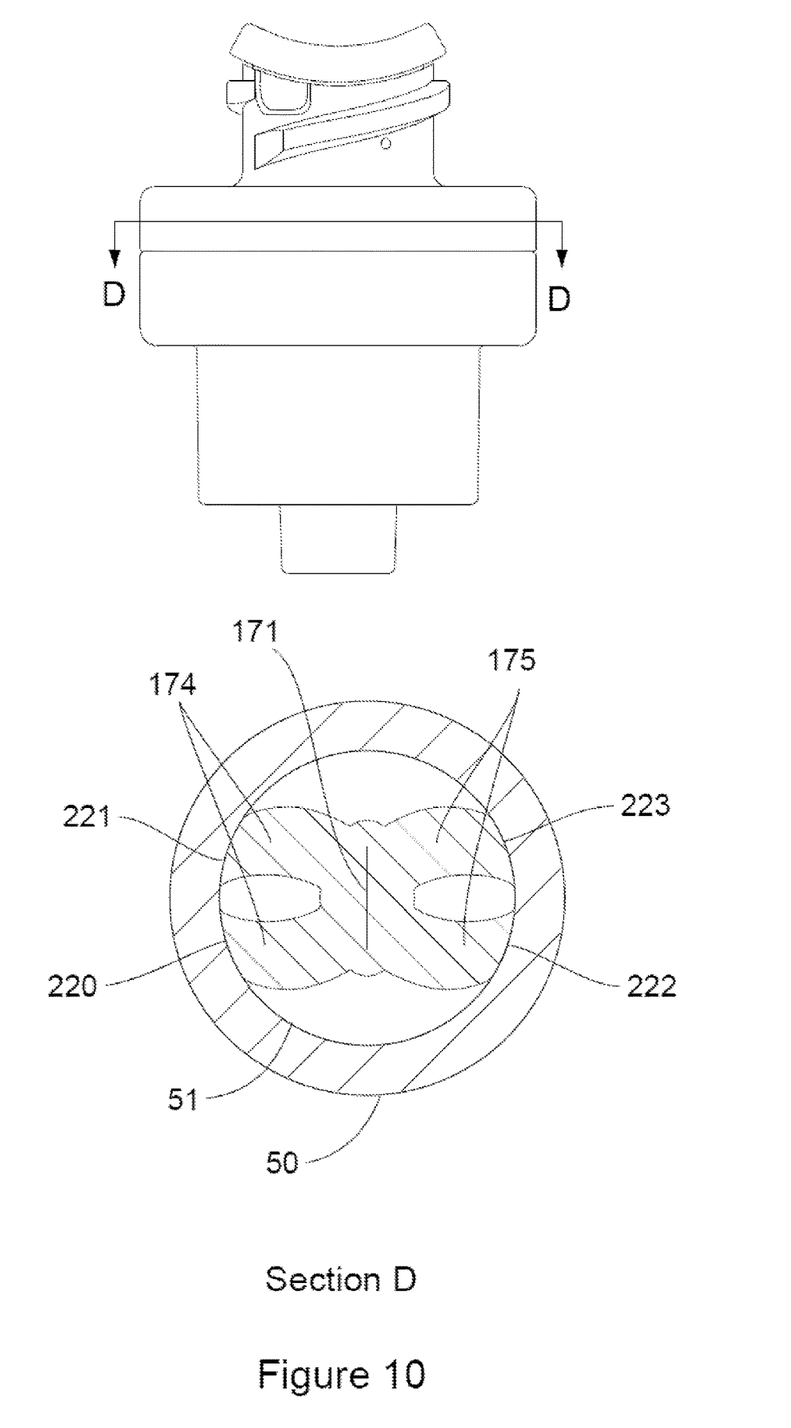
FIG. 10 shows a side view of the luer valve and longitudinal sectional view through section D-D of the septum.

As shown in FIG. 10 surfaces 220, 221, 222 and 223 are configured to abut an inner surface 51 of housing 50. Columns 174 and 175, with the septum 150 outside of housing 50, are longer from the centroid of septum 150 than the distance from the centroid of housing 50 to surface 51. Surface 51 of housing 50 could be a range of diameters with the diameter of the preferred embodiment being approximately 0.400 inches in diameter. Columns 174 and 175, with the septum 150 outside of housing 50 could have a range of diametral extents with the diameter of the preferred embodiment being approximately 0.460 inches in diameter.

Thus, in the preferred embodiment there is approximately 0.030" of interference between columns 174 and 175 of septum 150 to inner surface 51 of housing 50. In this manner when septum 150 is placed inside housing 50 surfaces 220, 221, 222 and 223 will compress against surface 51 of housing 50 and create a force generally normal to slit 171. Said force acts to close slit 171 and in combination with the duckbill action of curved surface 182 (FIG. 6) prevents escape of fluids from the hollow central core 177 (FIG. 6).

The amount of interference can clearly be understood to vary in accordance with the desired amount of pressure designed to be induced on slit 171 by the interference between columns 174 and 175 as measured at the location of abutment of surfaces 220, 221, 222 and 223 against inner surface 51 of housing 50.

Referring to FIG. 2, one advantage of this configuration is achieved by the longitudinal mass of the elastomeric support columns 174 and 175, which will tend to carry lateral movement of the septum downward. When the advancing luer 20 collapses the columns 174 and 175, the elastic laterally directed force of the collapse is carried longitudinally along the distal aspect of the slit 171 and this enlarges the size of the distal opening of the slit 171 beyond distal end 21 of the luer 20 to open the slit 171. This column deflection below the distal end of the luer 20 enhances the elastomeric space of hollow core 178 below the fully advanced luer 20.

In the preferred embodiment, the distal end 21 of luer 20 fails to reach hollow core 178 when maximally advanced so that the distal opening of the slit 171 beyond distal end 21 of the luer 20 and the enhancement of hollow core 178 are reliably present. (The formation of an elastomeric flow space within a septum below the fully advanced luer is discussed in U.S. Pat. No. 6,171,287 of the present inventor.) The hollow core 178 is enlarged when the luer 20 is fully advanced and rebounds to reduce in size when the luer 20 is retracted thereby mitigating or eliminating any negative pressure deflection in a flow channel 105 of housing 100. The flow channel of inner tube 105 is configured such that it is easily flushed by fluid from the luer by being similar in size to hollow core 178 and located immediately adjacent to hollow core 178. The relationship in size between flow channel 105 and hollow core 178 is advantageous in mitigating the undesirable affects of dead volume within the valve. If desired a flow deflector (not shown) to induce turbulent flow within the flow channel can be provided.

Figure 11:
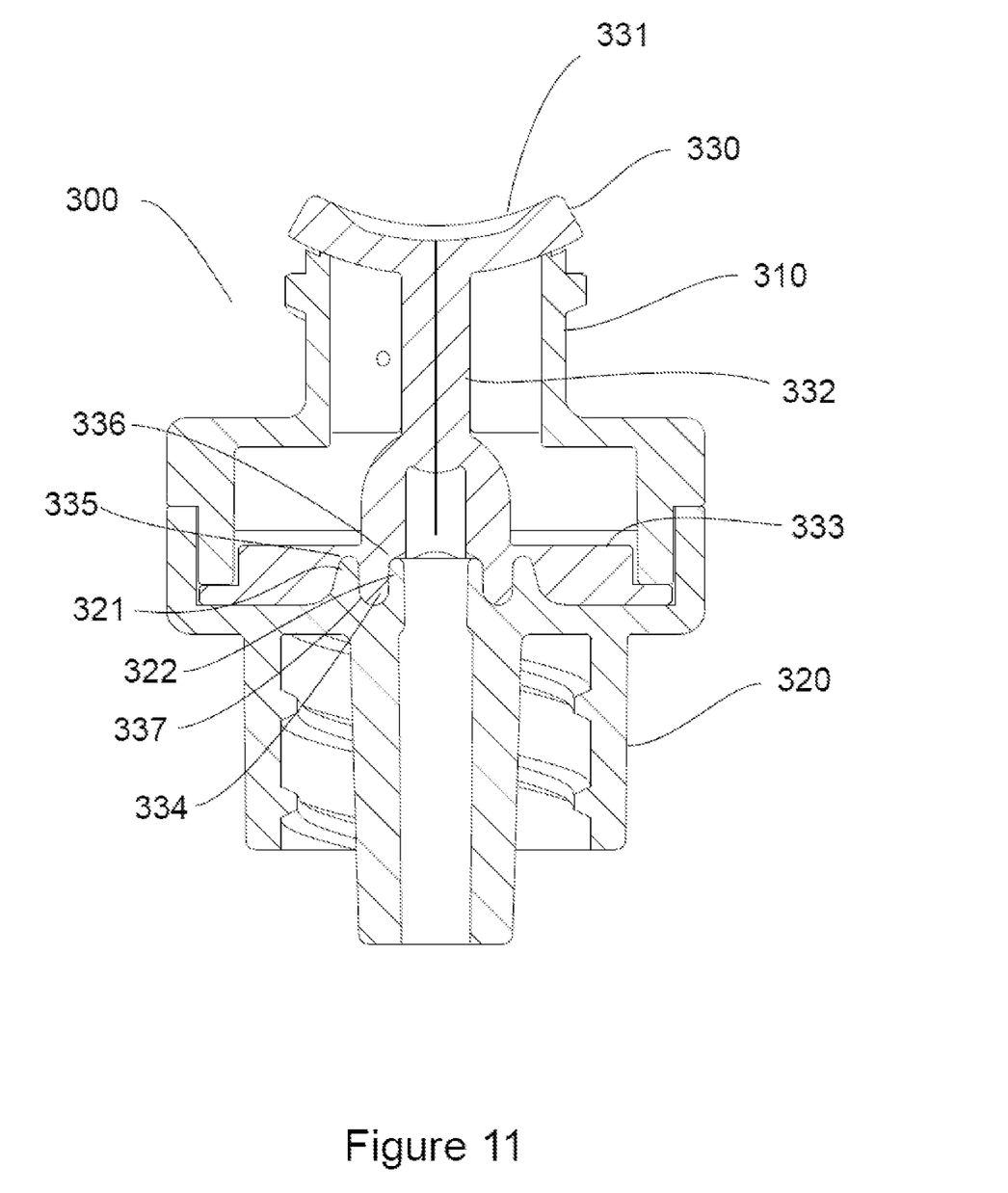
FIG. 11 shows a longitudinal section view of a split septum luer receiving valve according to an embodiment of the present invention.

FIG. 11 discloses an alternative luer receiving valve 300 which includes a proximal outer housing 310 and a distal outer housing 310 and an elastomeric septum 330. The elastomeric septum 330 includes an upper portion 310, an extension 332 and a lower portion 333. The lower portion 333 is seated on a surface of housing 320 with a first annular projection 321 and second annular projection 322 which mate to a first receiving annular recess 335 and a second receiving annular recess 336 of lower portion 333. Lower portion 333 further comprises an elastomeric annular projection 334 that is a circularly columnar projection of extension 332. Annular projection 321 and 322 are similar in profile to annular recesses 335 and 336 such that when mated a seal 337 is effected along the interface of the mating surfaces. Variations of the profile of annular recesses 335 and 336 of septum 330 and annular projections 321 and 322 of housing 320 may be incorporated in order to create an interface of dissimilar characteristics such as shape, diameter, location, surface texture, etc., such that when mated together the rigid nature of annular projections 321 and 322 can induce higher normal forces at their interface to recesses 335 and 336 of septum 330 and a correspondingly higher seal effect at and along seal 337. In a preferred embodiment of the present design the cavity between annular projections 321 and 322 is smaller than the size of projection 334 such that when assembled together projections 321 and 322 exert a compressive force against projection 334 and increase the seal effect of 337. The interface and general profile of the projections and recesses can further be refined to include appropriate angularity of mating surfaces to aid in general assembly of the components in a manufacturing setting.

Figure 12:
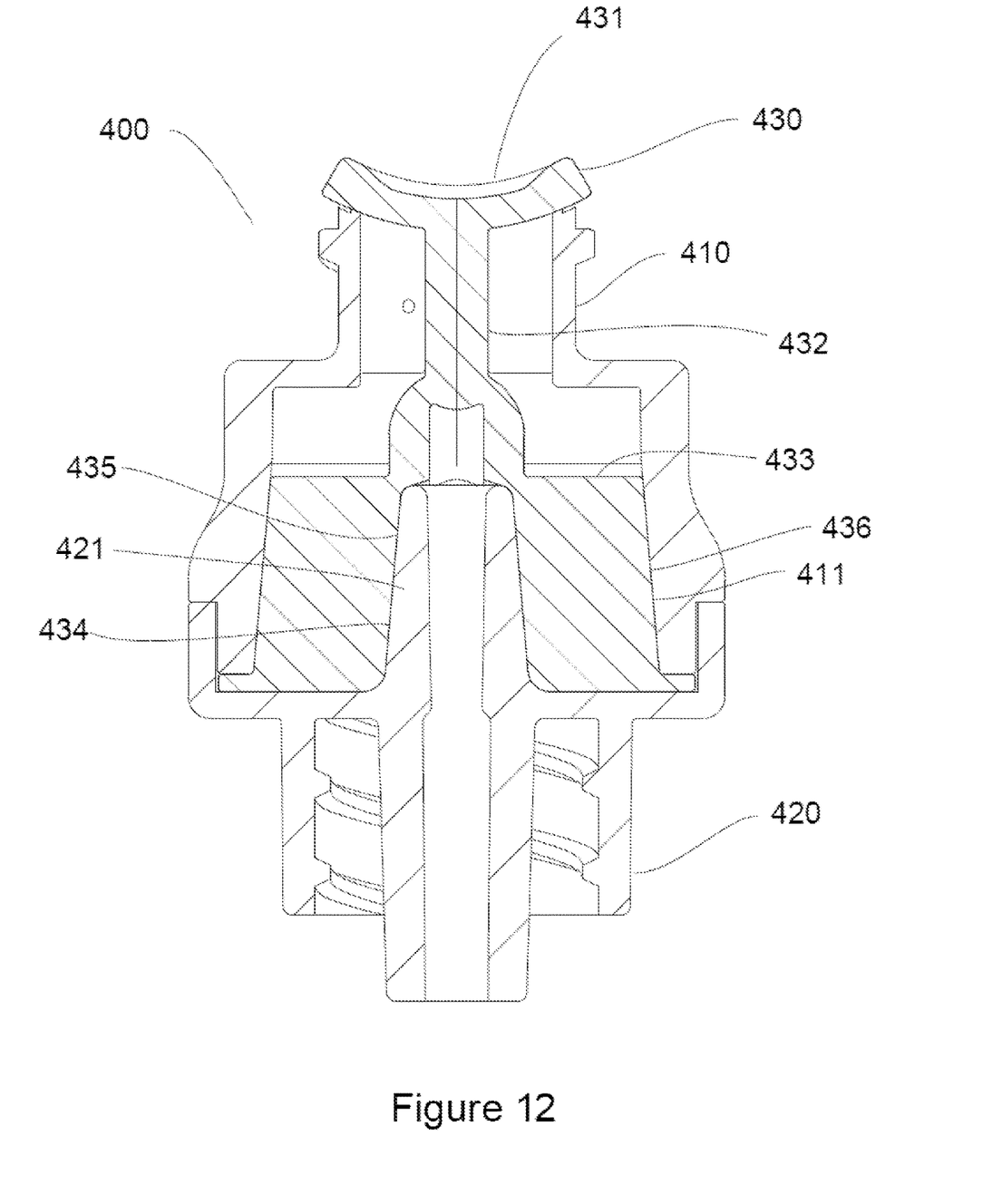
FIG. 12 shows a longitudinal section view of a split septum luer receiving valve according to another embodiment of the present invention.

FIG. 12 discloses a further alternative design for a luer receiving valve. In order to increase normal forces and resultant sealing effect between the septum and distal housing the interface of the septum and distal housing have been increased as will be described. An alternative luer receiving valve 400 includes a proximal outer housing 410 and a distal outer housing 420 and an elastomeric septum 430. The elastomeric septum 430 includes an upper portion 431, an extension 432 and a lower portion 433. The lower portion 433 is seated on a surface of housing 420 with an annular projection 421 which mates to a receiving annular recess 434 of lower portion 433. A seal area 435 is effected at the interface of projection 421 and recess 434. Variations can be made of the characteristics of projection 421 and or recess 434 including diameter, shape, surface texture, etc., in order to increase sealing forces of seal area 435. Further enhancement of seal area 435 is derived from the interface of a surface 411 of proximal outer housing 410 to a corresponding surface 436 of lower portion 433 of septum 430. Lower portion 433 is generally cylindrical in nature and is sized in such a manner that it is larger than the similarly cylindrically shaped space afforded it by the proximal outer housing 410. Thus in a manufacturing process when septum 430 is housed within proximal outer housing as seen in FIG. 12, the outer housing circumferentially displaces a volume of the elastomeric material of lower portion 433 with force being correspondingly exerted radially inwardly on lower portion 433 such that further increased normal forces are incurred at and along seal area 435. The interface and general profile of the projection, recess and other surfaces can further be refined to include appropriate angularity of mating surfaces to aid in general assembly of the components in a manufacturing setting.

Figure 13:
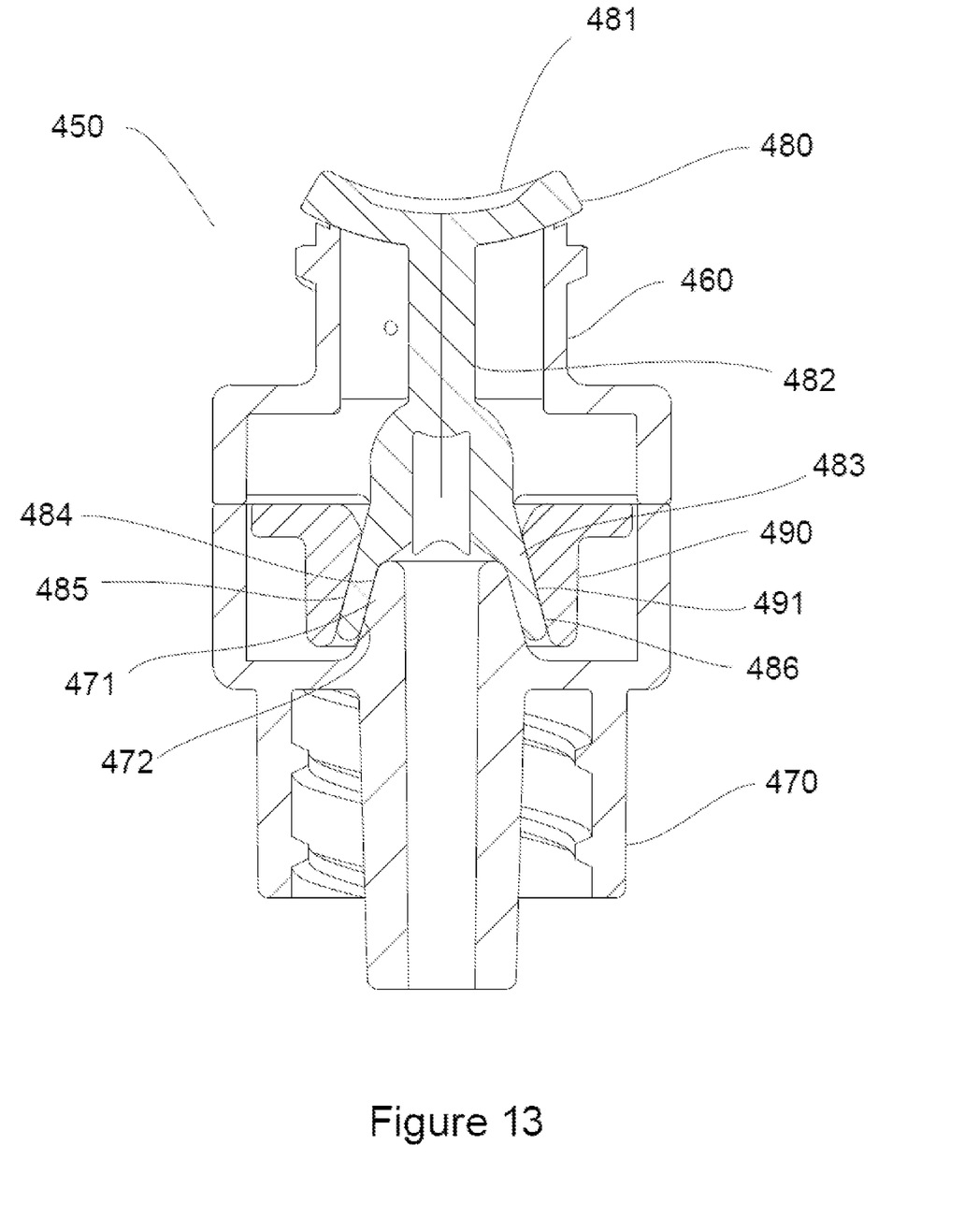
FIG. 13 shows a longitudinal section view of a split septum luer receiving valve according to another embodiment of the present invention.

FIG. 13 discloses another variation of a luer receiving valve. The valve 450 has a proximal outer housing 460 a distal outer housing 470 and a septum 480. The septum 480 has an upper portion 481, an extension 482 and a lower portion 483. A ring 490 is further incorporated into the design which ring 490 generally lies adjacent the lower portion 483 of the septum. The lower portion of the septum 483 is conical having an inner conical tapered surface 484 and an outer conical tapered surface 485. Correspondingly the distal outer housing 470 has a surface on which is an annular projection 471. Annular projection 471 is frusto-conical in shape and has an outer surface 472 which is similar in profile to that of inner conical tapered surface 484 of the lower portion 483 of septum 480. Ring 490 has a conical tapered surface 491 which is similar in profile to both that of annular projection 471 and the outer conical tapered surface 485 of lower portion 483 of septum 480. In this manner when ring 490 is placed about lower portion 483 and septum 480 creating a subassembly and this subassembly is placed on annular projection 471 of distal outer housing 470 a tight seal 486 is created at the interface. The inner conical taper 484 and frusto-conical annular projection 471 (having an upwardly tapering outer wall) are designed as an outer elastomeric tube and an inner tube, respectively, to aid in general assembly of their parent components in a manufacturing setting as well as to have low initial normal forces during assembly with maximum normal forces when the components are fully seated one to another.

Figure 14:
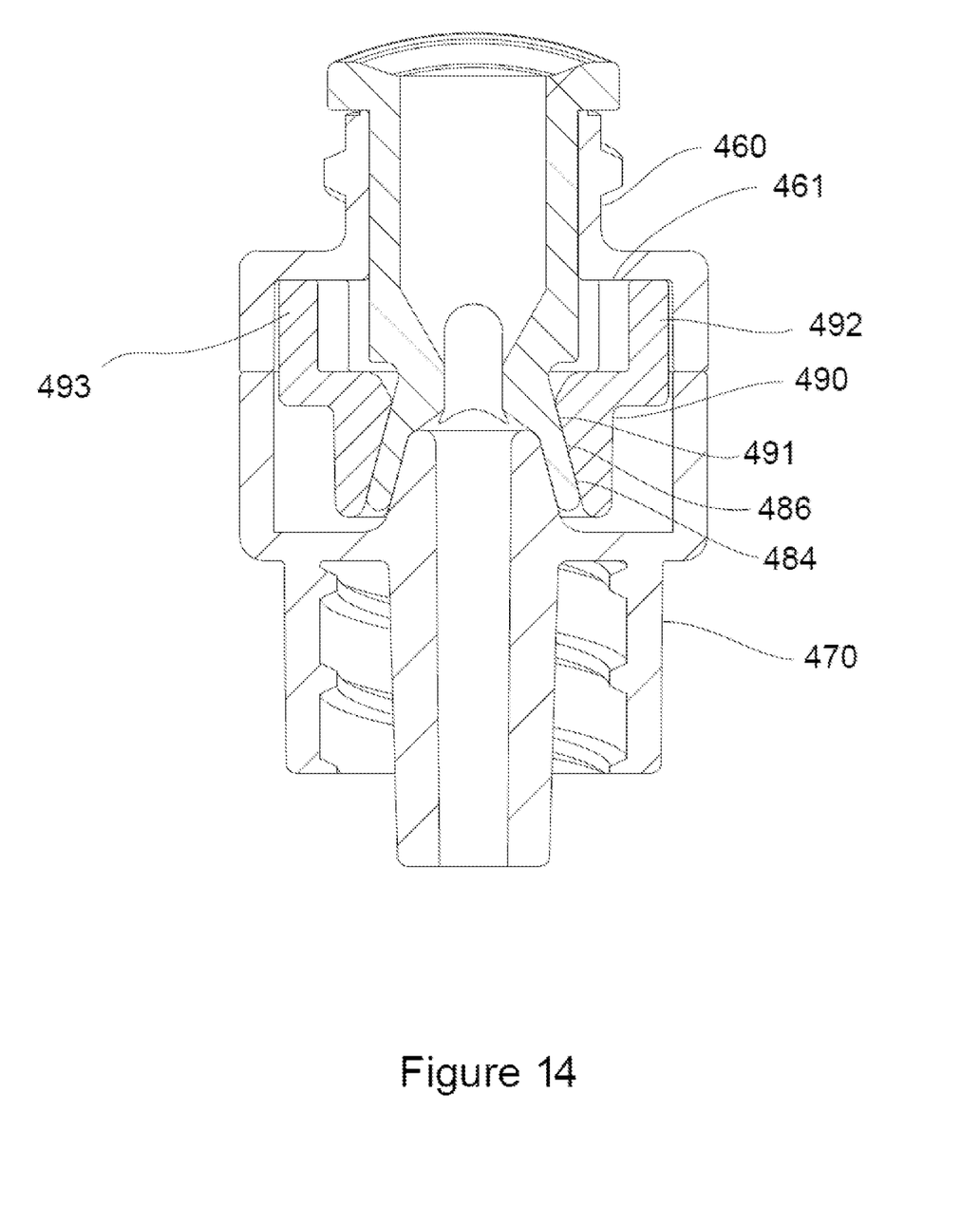
FIG. 14 shows a longitudinal section view of a split septum luer receiving valve according to another embodiment of the present invention.

FIG. 14 is a cross sectional view of luer receiving valve 450 which view is 90 degrees rotated from the cross sectional view of FIG. 13. In this view the ring 490 is seen to have projections 492 and 493. Projections 492 and 493 project upwards in a manner in which they abut an interior face 461 of proximal outer housing 460. In an assembled state outer housing 460 is connected to distal outer housing 470 via sonic welding or adhesive or any of several known methods of connecting rigid plastic components one to another. As proximal outer housing 460 is driven towards and comes to rest on distal outer housing 470 the ring 490 with projections 492 and 493 which abut an interior face 461 of proximal outer housing 460 is subsequently also driven in a like direction. This directed placement of ring 490 creates and maintains a force directed towards the seal area 486 via conical taper 491 of ring 490 and conical taper 484 of septum 480.

It will be understood that while the invention has been described in conjunction with various embodiments and details thereof, the foregoing description and examples are intended to illustrate, but not limit the scope of the invention. Numerous other variations and arrangements are within the scope of the invention as defined in the appended claims.

The invention claimed is:

1. A luer receiving valve for receiving a male luer mounted within a threadable luer lock connector shroud, the valve comprising: a luer valve housing having a channel for fluid passage and an inlet, an outlet, the housing having a proximal portion sized to be received into the luer lock connector shroud adjacent the inlet, and a distal portion having at least one transversely enlarged chamber defining at least one internal wall, the chamber having a diameter greater than the shroud, a septum positioned within the channel, the septum defining an upper portion with an outer face mounted adjacent the inlet, and a plurality of elastomeric columns projecting laterally within the chamber, and a lower sealing portion in sealing contact with the distal portion, the septum further having a central slit through the face, the slit being configured to allow insertion and penetration of the male luer into the central slit.

2. The luer receiving valve of claim 1, wherein each elastomeric column defines a longitudinal axis and is under compression along the longitudinal axis induced by the internal wall.

3. The luer receiving valve of claim 2, wherein the elastomeric columns are configured to be compressed against the internal wall of the chamber upon insertion of the male luer and to deflect the septum centrally, forcefully sealing the central slit, after the male luer has been removed from the central slit.

4. The luer receiving valve of claim 3, wherein each elastomeric column is under sufficient compression along the longitudinal axis induced by the internal wall so that the column strength along said axis of each of the elastomeric columns is reduced but the slit sealing force is high.

5. The luer receiving valve of claim 4, wherein the elastomeric columns comprise opposing pairs of elastomeric support columns supporting the central slit in the forcefully sealed position.

6. The luer receiving valve of claim 5, wherein each elastomeric column is configured to bow outwardly prior to insertion of the male luer.

7. The luer receiving valve of claim 5, wherein each elastomeric column is configured to bow outwardly upon insertion of the male luer.

8. The luer receiving valve of claim 6, wherein each elastomeric column is configured to spring inwardly upon of the withdrawal of the male luer.

9. The luer receiving valve of claim 5, wherein the elastomeric columns are bowed outwardly at rest to reduce the column strength along said axis of the columns and to thereby facilitate collapse of the columns on compression of the columns induced by the insertion of the male luer into the slit.

10. The luer receiving valve of claim 5, wherein the elastomeric columns define a laterally projecting gap between the columns.

11. The luer receiving valve of claim 10, wherein the gap is configured to enlarge and allow movement of elastomeric material when the male luer is inserted into central slit.

12. The luer receiving valve of claim 1, wherein the distal portion comprises a rigid flow channel adjacent the outlet and the lower sealing portion is positioned in sealing contact about the flow channel.

13. The luer receiving valve of claim 4, wherein the distal portion comprises a rigid flow channel adjacent the outlet and the lower sealing portion is positioned in sealing contact about the flow channel.

14. The luer receiving valve of claim 1, wherein there are at least four elastomeric columns projecting laterally within the chamber.

* * * * *